United States Patent [19]

Grabendorfer et al.

[11] 4,065,960
[45] Jan. 3, 1978

[54] METHOD AND APPARATUS FOR MONITORING THE OPERATION OF ULTRASONIC TESTING OF TUBES AND BARS

[75] Inventors: Werner Grabendörfer, Bensberg-Refrath; Herbert Vogt, Burgwedel; Harri Haacke, Dusseldorf; Harry Kühn, Langenfeld; Reinhard Pawelletz, Erkrath-Unterbach; Karl Ries, Mulheim, all of Germany

[73] Assignees: Krautkramer GmbH, Cologne; Mannesmann Aktiengesellschaft, Dusseldorf, both of Germany

[21] Appl. No.: 749,603

[22] Filed: Dec. 13, 1976

[51] Int. Cl.² .............................. G01N 29/04
[52] U.S. Cl. ........................... 73/627; 73/629
[58] Field of Search ............... 73/67.7, 67.8 R, 67.8 S, 73/67.9

[56] References Cited
U.S. PATENT DOCUMENTS 3,685,348 8/1972 Bottcher et al. ............ 73/67.8 R 3,888,114 6/1975 Adams et al. ............... 73/67.8 R

FOREIGN PATENT DOCUMENTS 812,331 4/1959 United Kingdom ............ 73/67.7

Primary Examiner—Richard C. Queisser
Assistant Examiner—John P. Beauchamp
Attorney, Agent, or Firm—Ervin B. Steinberg; Philip J. Feig

[57] ABSTRACT

This invention relates to immersion ultrasonic pulse-echo testing of tubes or bars for internal defects wherein means are provided to continuously monitor the operation of the test channel. As ultrasonic energy enters the workpiece, the round workpiece surface causes acoustic energy scatter responsive echo signals which are sensed by the transmitter probe, are amplified and applied to a threshold circuit. If the amplitude of the scatter responsive signal falls below a predetermined level, an output signal indicative of "loss of operation" is produced. Means are provided to inhibit such output signal in the event of only a momentary decrease of the scatter responsive signal below a predetermined value.

22 Claims, 14 Drawing Figures

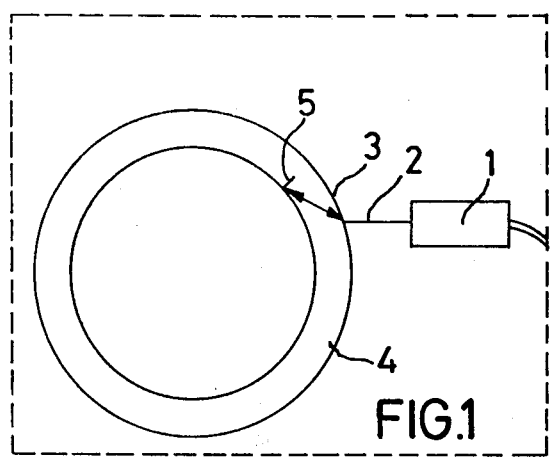
FIG.1
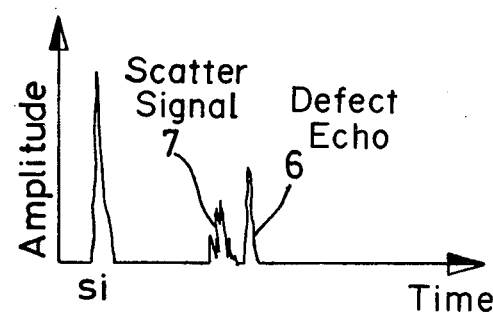
FIG.4
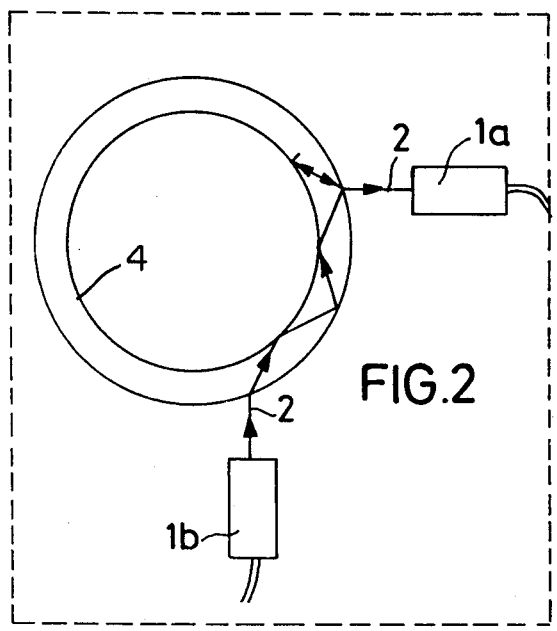
FIG.2
FIG.3
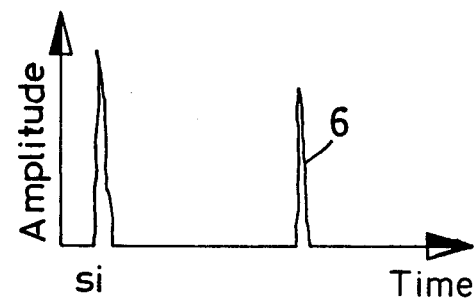
FIG.5
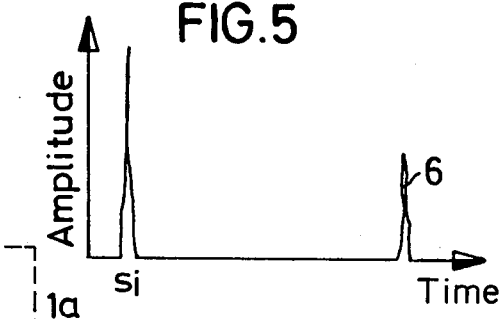
FIG.6

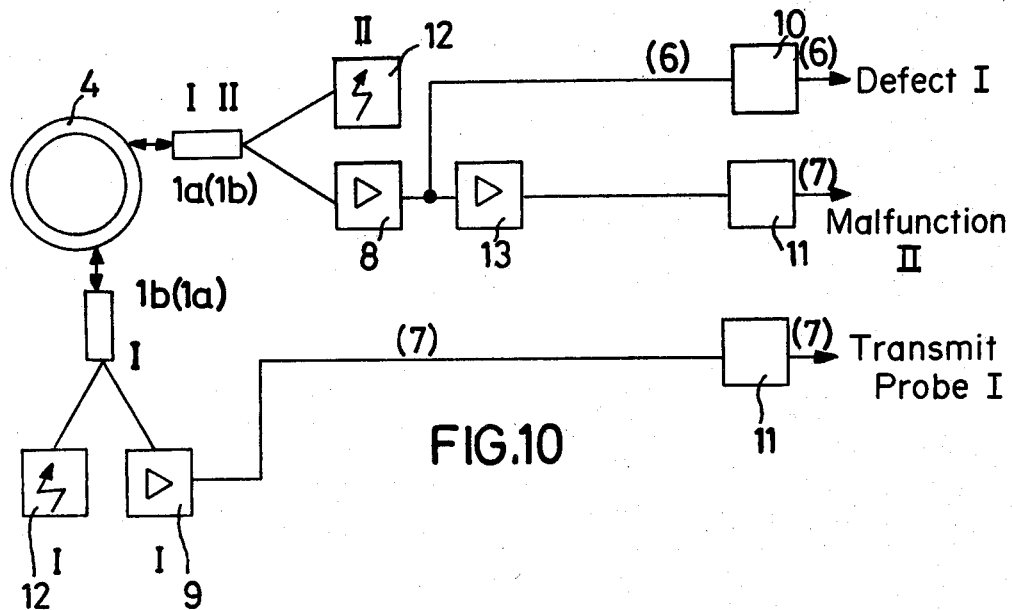
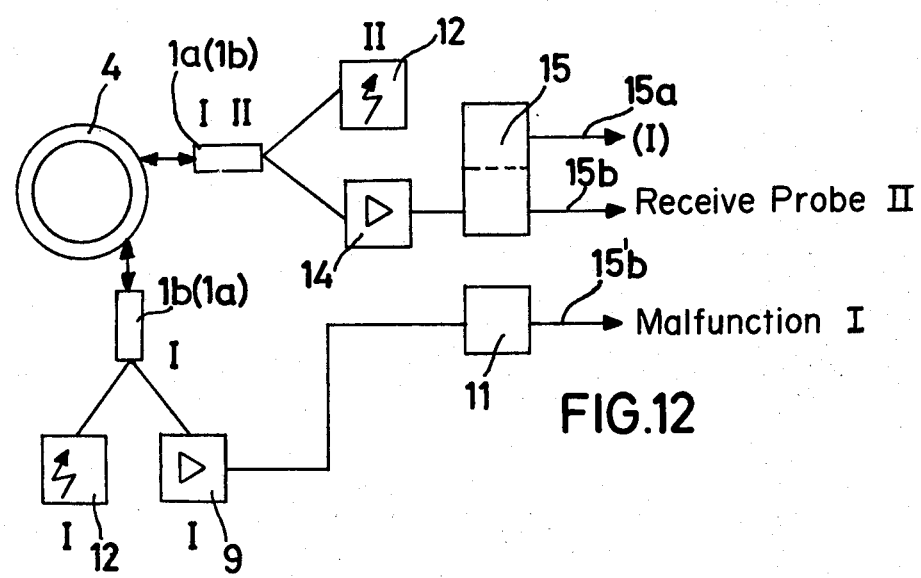
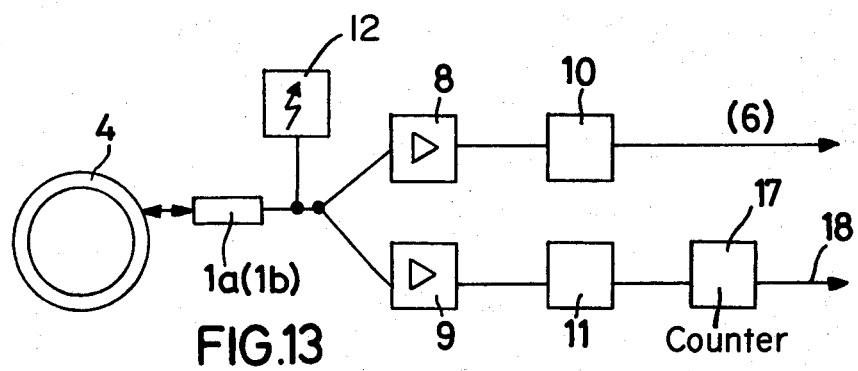

METHOD AND APPARATUS FOR MONITORING THE OPERATION OF ULTRASONIC TESTING OF TUBES AND BARS

FIELD OF INVENTION

This invention concerns a method and apparatus for monitoring the operation of one or of a plurality of transmit transducer probes and/or of amplifiers when testing tubes and bars by the ultrasonic immersion pulse-echo test method. The invention particularly concerns the monitoring of the electro-acoustic apparatus when testing workpieces for cracks in proximity to the surface.

BRIEF SUMMARY OF THE INVENTION

Ultrasonic immersion test arrangements are known for the purpose stated above wherein one or two test probes are disposed in a plane normal to the tube or rod axis and wherein the sound beams are incident via a water path upon the workpiece surface at an angle from about 14° to 27° from normal; the water serving as a coupling path. When a single test probe is used, such probe operates as a transmitter as well as a receiver for the ultrasonic energy. When two test probes are used, one probe operates as the transmitter and the other as receiver of the ultrasonic energy. Preferably in the latter case, the position of the receiver test probe is advanced relative to the rotation of the tube axis by 90° or 180°. The two-test probe arrangement is particularly advantageous when rough workpiece surfaces are present since in this case substantially none or only a small portion of the sound beam is reflected back by reflection at the workpiece surface to the receiver test probe. In this manner, it is possible to evaluate test signals (defect echoes) without interference from the surface induced signals.

However, these test systems cannot be monitored continuously for proper operation since, in accordance with their operational principle, they lack a reference signal, for example a rear wall echo signal.

For checking the test apparatus it is necessary to test at regular intervals for comparison a workpiece having a known defect. Continuous monitoring of the operation during the progress of the test process is not possible with the known arrangements. This fact is particularly disturbing since these test methods are used largely in fully automatic ultrasonic test systems. Moreover, for increasing the test speed frequently several test systems are operated in parallel, performing the same test function and, hence, an urgent need exists to monitor on a continuing basis the faultless operation of the several test channels operating in parallel. As understood herein a test channel is defined as the operating chain comprising the electronic pulse generator, transmit probe, receiver probe and amplifier.

This invention deals with the problem of providing a method for continuously monitoring the operation of a test system as noted above.

The invention is based on the fact that when an ultrasonic energy angle beam is transmitted into a curved workpiece surface, scattered reflections are always produced, such reflections being more or less prominent, but always present during the relative helical scan motion of workpieces.

These scattered signals are produced in a known manner resulting from surface roughness and are present on account of the beam width of the entering sound beam and because of the curvature of the tube surface during a certain portion of the transit time.

The novelty of the present invention resides in the feature that the absence of the scatter responsive signals, which regularly are visible on the cathode ray tube screen as a burst of spurious signals, is evaluated as a disorder in the respective test channel.

For practicing the invention, it is significant therefore, to extract the burst of scatter responsive echo signals and to amplify and monitor those signals. Switch means are used to preclude a momentary absence of these signals, e.g., two or three times, to be registered as an operational disorder.

In accordance with the present invention, means are provided for receiving at test probes the sound scatter responsive signals arising by reflection at the tube or bar surfaces and to amplify and pass the signals through a gate, and moreover, to signal as an operation disturbance the condition when the scatter responsive signals decrease below a predetermined threshold value.

The instant invention will be more clearly apparent by reference to the following description when taken in conjunction with the accompanying drawings.

BRIEF DESCRIPTION OF THE DRAWINGS

FIGS. 1 through 3 depict known immersion test arrangements;

FIGS. 3 through 6 depict the echo signal indications (for instance inside lengthwise defect) pertaining to FIGS. 1 through 3;

FIGS. 9 and 10 disclose arrangements for monitoring the operation utilizing scatter indication and the inclusion of defect signal amplifiers in the monitor circuit.

FIGS. 11 and 12 disclose arrangements for monitoring the operation utilizing scatter indication and inclusion in the circuit of defect signal amplifiers in a single monitor system.

FIG. 13 shows a safety circuit to inhibit faulty signals, and

DETAILED DESCRIPTION OF THE INVENTION

Figure 7:
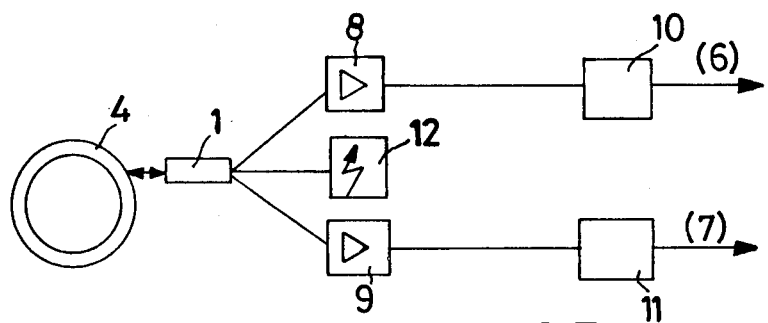
FIGS. 7 and 8 disclose arrangements for monitoring the operation utilizing scatter indication.

FIGS. 1 through 6 depict the known immersion test arrangements with their respective echo representation, in the present example an inside axial defect. An ultrasonic beam 2 transmitted from the transmit-receive test probe 1 enters the surface 3 of a workpiece 4, e.g., a tube, and after reflection at a defect 5 is reflected back toward surface 3 and is manifest as an amplitude peak 6 adjacent to a scatter signal 7 on a cathode ray tube screen as shown in FIGS. 4 and 6. The first peak $S_i$ denotes the transmit pulse responsive signal.

One embodiment of the invention is shown in FIG. 7 which discloses aside from the amplifier 8 used for defect signal evaluation also a second amplifier 9 coupled in parallel, the latter providing a relatively greater amplification. Therefore, the amplifier 9 is capable of providing continuously a scatter responsive echo signal of sufficient output signal amplitude. The circuit depicts, in addition, a set of monitors 10 and 11 for the defect responsive signal and the scatter responsive signal respectively. An ultrasonic pulse generator 12 cyclically produces the transmit pulse signal as is well understood in the art of ultrasonic testing.

Figure 8:
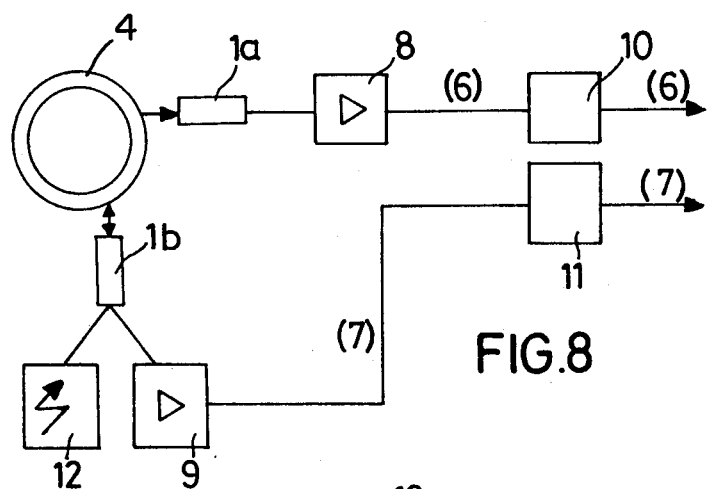

In a second and third embodiment, see FIGS. 2, 3 and 8, the same result is achieved if the transmit probe 1b is coupled also to an amplifier 9 which amplifies the surface induced scatter responsive echo signals that are reflected back to the transmit probe 1b, whereas the amplifier 8 coupled in circuit with the receive probe 1a amplifies the defect responsive signals. The gain of the amplifiers 8 and 9 can be adjusted independently from each other.

It has proven advantageous to include the defect signal amplifiers in the monitoring circuit.

Figure 9:
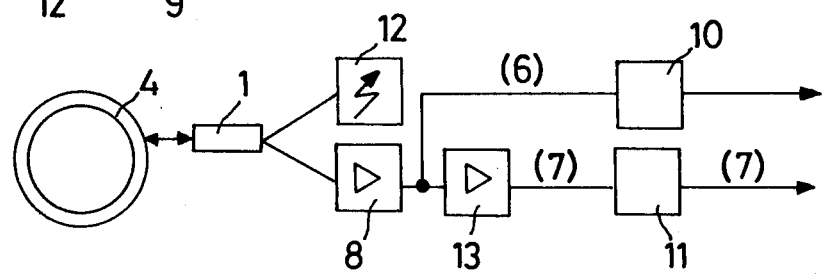
Figure 11:
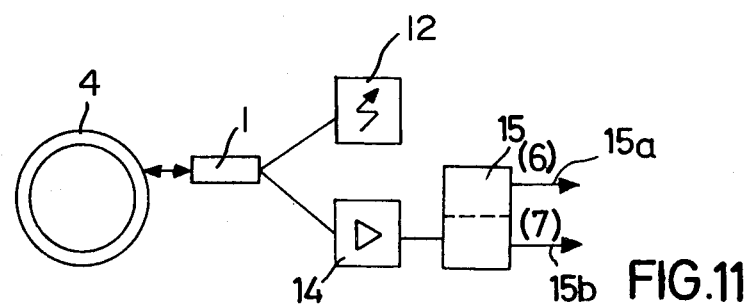

To this end, the arrangements shown in FIGS. 7 and 8 can be improved. Specifically, the heretofore shown arrangements do not include the defect responsive signal amplifiers in the monitoring circuit. This disadvantage can be remedied by providing after the defect signal amplifier 8 a further amplifier stage 13 for amplifying the scatter responsive signals, see FIG. 9. In accordance with another embodiment, see FIG. 11, a single amplifier 14 having a logarithmic gain characteristic is used for providing both of the monitoring functions. The output signal from the amplifier 14 is coupled to a monitor system 15 which is adjusted for two different threshold values. For instance, signal 15a is the "defect signal" and is generated when a defect responsive signal exceeds a first threshold value, and signal 15b is the "loss of operation" signal and is produced when the scatter responsive signal is less than a predetermined second threshold value. Since an amplifier with a logarithmic gain characteristic has such a large dynamic range, it is possible to evaluate both signal indications, i.e., defect and scatter indications, at the output of the amplifier with two differently adjusted threshold values, especially in view of the fact that both signals frequently exhibit a considerable difference in signal amplitude.

In conjunction with the embodiments per FIGS. 2 and 3 in addition to the amplifier 13 for the scatter responsive signals a further monitor cycle is required in order to test the operation of the defect responsive signal amplifier 8. During the first time cycle (I), see FIGS. 10 and 12, the transmit probe 1b operates as transmitter as is normally the case. The other probe 1a operates as receiver for defect responsive echo signals 6 and the transmit probe 1b operates also for receiving the scatter responsive signals 7. During the following cycle (II), which serves merely for monitoring the operation of the defect signal amplifier 8, the receive transducer probe 1b operates as transmitter 1a and the ensuing scatter responsive signals 7 are amplified by the defect signal amplifier 8 and then further amplified in an amplifier 13 for causing the scatter responsive signals to be rendered capable of being monitored and evaluated. Instead of the last-mentioned combination, once again a logarithmic gain amplifier 14 can be used as stated previously in conjunction with the embodiment per FIG. 11. In this event, see FIG. 12, during the test cycle I, the defect responsive output signal 15a from the threshold device 15 is used for defect evaluation and the scatter absent signal 15'b indicating a malfunction would be apparent at the output of monitor 11. During the ensuing monitor cycle II when the previous receive probe 1a becomes a transmitting probe, the scatter responsive signal received by the transmitting probe is fed via the logarithmic amplifier 14 to the threshold device 15 for causing in the event of a malfunction a scatter absent signal 15b. Hence, the condition of signal 15b is used for monitoring the operation of the defect echo signal channel.

With reference to FIG. 13, in order to prevent the condition that a single, very brief, lack of the scatter indication 7 is registered as an operational fault, it is possible to include in all of the arrangements a suitable inhibit circuit. A counting circuit 17 coupled after the monitor circuit 9 achieves this result by providing that only after an adjustable, predeterminable number of sequential failures, i.e., failure of the scatter signals to reach the threshold level, a signal 18 is produced, the presence of which serves to indicate lack of proper operation, see FIG. 3 in conjunction with the embodiment per FIG. 10. As is apparent to those skilled in the art, the counting circuit must cyclically be reset.

Figure 14:
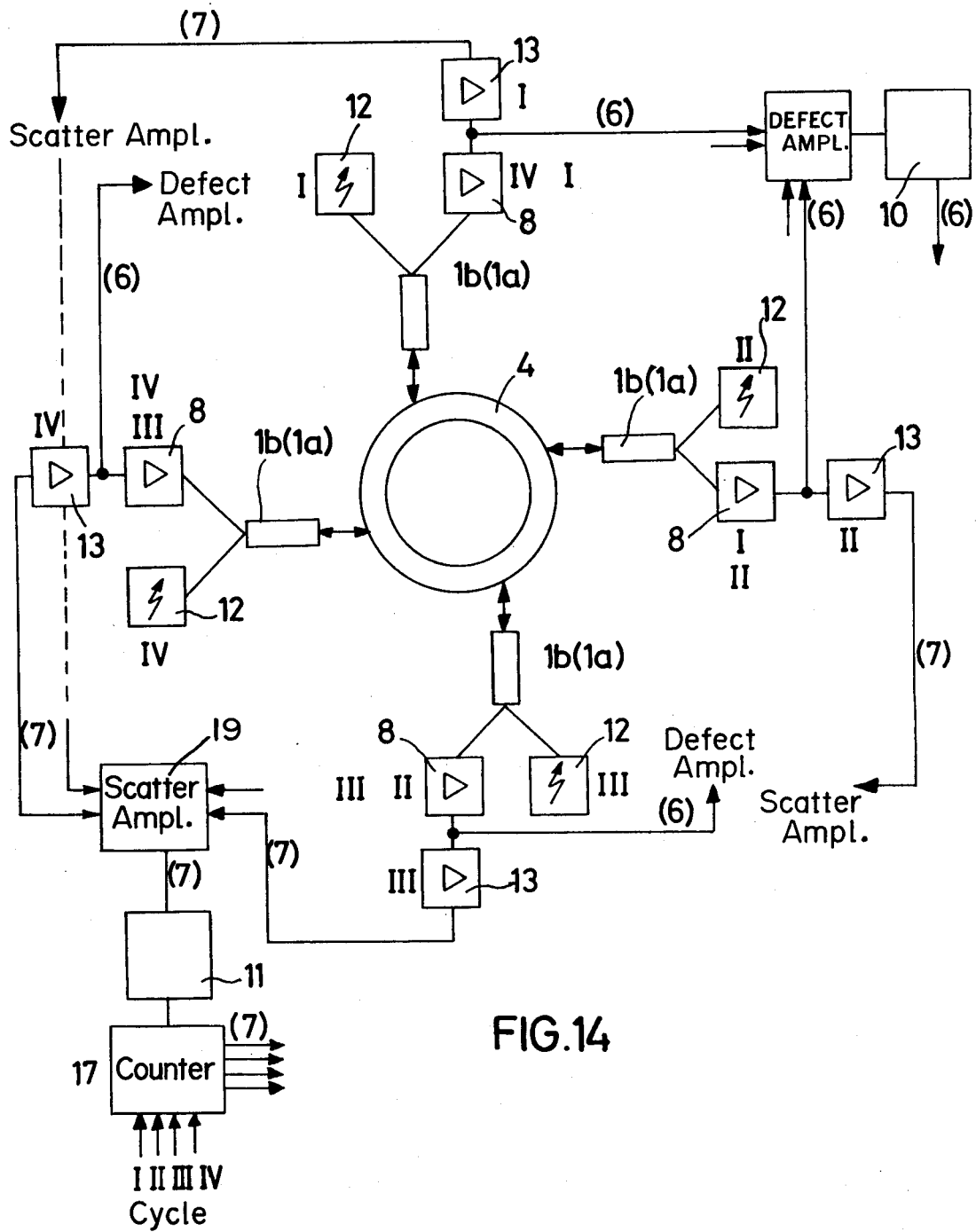
FIG. 14 is a schematic diagram for multi-channel test apparatus.

If, as shown in FIG. 14, several independently operating test channels are present, the monitoring function can be achieved by multiplication of the previously described circuits. However, particularly in connection with the arrangement shown per FIG. 2, multi-channel systems are known which do not operate independently of one another. For the arrangement, shown for instance in German patent publication OS No. 21 38 458.7, there are provided four test probes 1a and 1b which are disposed equidistantly about the circumference of the workpiece and which operate in accordance with the principle shown in FIG. 2. In accordance with the present invention an improvement, see FIG. 14, is provided to the effect that during cyclic testing at all times one pulse generator 12 is coupled in circuit with an associated test probe 1a, and the associated amplifier 8 coupled in series with a respective receive probe 1b is rendered operative for signal reception. Each of the four test probes, which are cyclically rendered operative by conventional means, not shown, operate therefore once as a transmitter 1b and once as a receiver 1a. The solution in accordance with the present invention of the problem to monitor the proper function of all elements comprising the test apparatus is achieved by utilizing the arrangement previously described in conjunction with FIG. 9. The cycle signals designated I, II, III and IV must be observed which are coupled to the individual test probe or probe pairs respectively, for periodically conditioning the probes for the monitoring and the testing cycle.

The fault signals can be coupled to an intermediate amplifier 19, to a monitor 11 and to a preset signal sequence counter 17 which is scanned during cycles I, II, III and IV (FIG. 14 bottom) to provide, depending on the circumstances, a fault alarm signal for each of the first, second, third or fourth test probe. An analogous circuit, of course, can be made also with amplifiers 14 having a logarithmic gain characteristic. The operation of such latter circuit is then similar to that described in conjunction with FIG. 12.

It will be apparent to those skilled in the art that the defect responsive monitors and the scatter responsive monitors used heretofore are controlled by time gates in the known manner in order to render the monitors operative during predetermined periods of the test cycle.

What is claimed is:

1. The method for monitoring one or more transmit transducer probes and amplifiers in an ultrasonic pulse-echo immersion test apparatus when testing tubes or round bars comprising:

transmitting cyclically a search pulse of ultrasonic energy through a liquid coupling path into a workpiece having a curved surface, the angle of incidence of said ultrasonic energy upon the workpiece surface deviating from normal to cause the search pulse to propagate in a circumferential direction in the workpiece;

sensing the occurrence of scattering acoustic energy arising from the scattering of said search pulse energy at the curved workpiece surface;

converting said scattered energy to an electrical signal and amplifying said electrical signal, and providing a signal when said scattered energy responsive electrical signal amplitude falls below a predetermined threshold value.

2. The method for monitoring as set forth in claim 1, and sensing also the occurrence of a defect responsive echo signal arising from the search pulse intercepting a defect in the workpiece, and amplifying the defect responsive echo signal to a lesser extent than the scatter responsive electrical signal.

3. The method for monitoring as set forth in claim 2, the extent of amplifying the scatter responsive electrical signal and the defect responsive echo signal being independently adjusted.

4. An apparatus for monitoring one or more transmit transducer probes and amplifiers in an ultrasonic pulse-echo immersion test apparatus used for testing workpieces, particularly tubes and round bars, comprising:

electroacoustic probe means adapted to be energized cyclically for transmitting through a liquid coupling path an ultrasonic energy search pulse signal into a workpiece having a curved surface and for subsequently receiving reflection responsive echo signals and providing corresponding electrical output signals, such search signal being incident upon the workpiece surface at an angle deviating from normal to the workpiece surface for causing the search signal to propagate in the workpiece in a circumferential direction;

pulse generating means coupled to said probe means for cyclically energizing said probe means;

amplifying means coupled to said probe means for receiving and amplifying scatter responsive signals arising from the ultrasonic search signal being scattered and reflected at the curved surface of the workpiece and for receiving and amplifying defect responsive echo signals arising from the search signal intercepting a defect in the workpiece, and evaluating means coupled to said amplifying means for receiving said scatter responsive signals and providing an output signal when the scatter responsive signals fail to attain a predetermined signal amplitude.

5. An apparatus as set forth in claim 4, and further evaluating means coupled to said amplifying means for receiving the defect responsive signals and providing a further output signal when the defect responsive signals exceed a predetermined signal amplitude.

6. An apparatus for monitoring as set forth in claim 5, said amplifying means comprising a pair of amplifiers, one for amplifying said scatter responsive signals and the other for amplifying said defect responsive echo signals; means for independently adjusting the gain of said amplifiers, and said amplifier for said scatter responsive signals providing a higher gain to signals processed thereby.

7. An apparatus for monitoring as set forth in claim 5, said evaluating means and said further evaluating means comprising signal threshold means.

8. An apparatus as set forth in claim 5, said probe means comprising a first probe for transmitting said search pulse signal and subsequently receiving said scatter responsive echo signals and a second probe for receiving said defect responsive echo signals.

9. An apparatus as set forth in claim 5, said amplifying means comprising a first and a second amplifier connected in series, the output of said first amplifier providing said defect responsive signals and the output of said second amplifier providing said scatter responsive signals.

10. An apparatus as set forth in claim 5, said amplifying means including an amplifier having a logarithmic gain characteristic.

11. An apparatus as set forth in claim 4, and inhibit means coupled to said evaluating means for inhibiting said output signal until the scatter responsive signals fail to attain said predetermined amplitude for a predetermined time interval.

12. An apparatus for monitoring one or more transmit transducer probes and amplifiers in an ultrasonic pulse-echo immersion test apparatus used for testing workpieces, particularly tubes and round bars, comprising:

first electroacoustic probe means adapted to be energized cyclically during a first cycle and disposed for transmitting through a liquid coupling path an ultrasonic energy search pulse signal into a workpiece at a first location thereof, the workpiece having a curved surface, and for receiving subsequently reflection responsive echo signals and providing corresponding electrical output signals, such search signal being incident upon the workpiece surface at an angle deviating from normal to the workpiece surface for causing the search signal to propagate in the workpiece in a circumferential direction;

second electroacoustic probe means disposed for receiving during said first cycle defect responsive echo signals from the workpiece arising from the search pulse transmitted by said first probe means intercepting a defect in the workpiece and providing defect responsive electrical output signals, and adapted during a second cycle to cyclically transmit through a liquid coupling path an ultrasonic energy search pulse signal into the workpiece at a second location and for receiving subsequently reflection responsive echo signals and providing corresponding electrical output signals, such search signal being incident upon the workpiece surface at an angle deviating from normal to the workpiece surface for causing the search signal to propagate in the workpiece in a circumferential direction;

pulse generating means coupled to said first and said second probe means for cyclically energizing said first and said second probe means during the respective first and second cycles;

first amplifying means coupled to said first probe means and operative for receiving and amplifying during said first cycle scatter responsive electrical signals responsive to said first probe means transmitting its respective search signal and providing a first amplified signal;

second amplifying means coupled to said second probe means and operative for receiving and amplifying during said first cycle said defect responsive electrical output signals, and during said second cycle receiving and amplifying scatter responsive electrical signals responsive to said second probe means transmitting its respective search signal, and providing respectively a second and third amplified signal, and evaluating means coupled to said first and second amplifying means for receiving said first and third amplified signals and providing an output signal when either of said first or third amplified signals fails to attain a predetermined signal amplitude.

13. An apparatus as set forth in claim 12, and further evaluating means coupled to said second amplifying means for receiving said second amplified signal and providing an output signal when said amplified signal exceeds a predetermined signal amplitude.

14. An apparatus as set forth in claim 12, said first and said second locations being spaced approximately 90° about the circumference of the workpiece.

15. An apparatus as set forth in claim 12, said first and second locations being spaced approximately 180° about the circumference of the workpiece.

16. An apparatus as set forth in claim 13, said second amplifying means including a first and a second amplifier connected in series, the output from said first amplifier producing during said first cycle said second amplified signal responsive to a defect and said second amplifier producing during said second cycle the third amplified signal responsive to scatter in response to the search pulse from said second probe means.

17. An apparatus as set forth in claim 13, said second amplifying means including an amplifier having a logarithmic gain characteristic.

18. An apparatus as set forth in claim 12, and inhibit means coupled to said evaluating means for inhibiting said output signal until the scatter responsive signals fail to attain said predetermined amplitude for a predetermined time interval.

19. An apparatus as set forth in claim 18, said inhibit means comprising counting means.

20. An apparatus for monitoring one or more transmit transducer probes and amplifiers in an ultrasonic pulse-echo immersion test apparatus used for testing workpieces, particularly tubes and round bars, comprising:

a plurality of electroacoustic probe means disposed at approximately equidistant locations around the circumference of the workpiece adapted to be cyclically energized during respective cycles for transmitting through a liquid coupling path respective ultrasonic energy search pulse signal into the workpiece, the workpiece having a curved surface, and for receiving subsequently reflection responsive echo signals and providing corresponding electrical output signals, such search signal being incident upon the workpiece surface at an angle deviating from normal for causing the search signal to propagate in the workpiece in a circumferential direction;

pulse generating means coupled to said plurality of probe means for cyclically energizing each of said probe means in predetermined sequence;

amplifying means coupled to said plurality of probe means operative for receiving and amplifying scatter responsive signals arising from a respective probe means transmitting a search pulse signal and providing a first amplified signal responsive thereto, and receiving and amplifying defect responsive signals arising from a search pulse signal transmitted by a probe means other than from the probe means receiving the scatter responsive signals and providing a second amplified signal responsive thereto, and evaluating means coupled to said amplifying means for receiving said first amplified signals and providing an output signal when one of said first amplified fails to attain a predetermined signal amplitude.

21. An apparatus as set forth in claim 20, and further evaluating means coupled to said amplifying means for receiving said second amplified signal and providing an output signal when said second amplified signal exceeds a predetermined signal amplitude.

22. An apparatus as set forth in claim 20, and inhibit means coupled to said evaluating means for inhibiting said output signal until said first amplified signals fail to attain said predetermined amplitude for a predetermined time interval.

* * * * *

UNITED STATES PATENT AND TRADEMARK OFFICE
CERTIFICATE OF CORRECTION

PATENT NO. : 4,065,960
DATED : January 3, 1978
INVENTOR(S) : Werner Grabendorfer et al It is certified that error appears in the above-identified patent and that said Letters Patent are hereby corrected as shown below:

Column 7, line 13, before "amplified" insert --second--.

Column 8, line 32, before "fails" insert --signals--.

Signed and Sealed this

Ninth Day of May 1978

[SEAL]

Attest:

RUTH C. MASON
Attesting Officer

LUTRELLE F. PARKER
Acting Commissioner of Patents and Trademarks